US011878022B2

(12) United States Patent
Shanmugam et al.

(10) Patent No.: US 11,878,022 B2
(45) Date of Patent: Jan. 23, 2024

(54) HYDROCHLOROTHIAZIDE COMPOSITIONS

(71) Applicant: Novitium Pharma LLC, East Windsor, NJ (US)

(72) Inventors: Muthusamy Shanmugam, East Windsor, NJ (US); Subramaniam Arunkumar, East Windsor, NJ (US)

(73) Assignee: Novitium Pharma LLC, East Windsor, NJ (US)

( * ) Notice: Subject to any disclaimer, the term of this patent is extended or adjusted under 35 U.S.C. 154(b) by 0 days.

(21) Appl. No.: 18/053,197

(22) Filed: Nov. 7, 2022

(65) Prior Publication Data

US 2023/0111273 A1    Apr. 13, 2023

Related U.S. Application Data

(63) Continuation-in-part of application No. 17/546,175, filed on Dec. 9, 2021, now abandoned.

(30) Foreign Application Priority Data

Dec. 10, 2020    (IN) .............................. 202041053842

(51) Int. Cl.
| | |
|---|---|
| *A61K 31/549* | (2006.01) |
| *A61K 9/00* | (2006.01) |
| *A61K 47/26* | (2006.01) |
| *A61K 47/02* | (2006.01) |
| *A61K 47/12* | (2006.01) |
| *A61K 47/36* | (2006.01) |

(52) U.S. Cl.
CPC .......... *A61K 31/549* (2013.01); *A61K 9/0056* (2013.01); *A61K 9/0095* (2013.01); *A61K 47/02* (2013.01); *A61K 47/12* (2013.01); *A61K 47/26* (2013.01); *A61K 47/36* (2013.01)

(58) Field of Classification Search
CPC .................................................... A61K 31/549
See application file for complete search history.

(56) References Cited

U.S. PATENT DOCUMENTS

| 2,809,194 A | 10/1957 | Novello et al. | |
|---|---|---|---|
| 4,981,852 A | 1/1991 | Ahn | |
| 2022/0184094 A1* | 6/2022 | Shanmugam | ............ A61K 9/10 |

FOREIGN PATENT DOCUMENTS

| EP | 0341774 A1 | 11/1989 | |
|---|---|---|---|
| MX | 354316 B | 2/2018 | |
| WO | WO-03059327 A1 * | 7/2003 | ........... A61K 31/404 |

OTHER PUBLICATIONS

Petri, Denise F.S. "Xanthan gum: A versatile biopolymer for biomedical and technological applications." J. Appl. Polym. Sci. (2015), pp. 1-13 of 13 (Year: 2015).*
Bercu et al., "Potential impurities in drug substances: Compound-specific toxicology limits for 20 synthetic reagents and by-products, and a class-specific toxicology limit for alkyl bromides", Regulatory Toxicology and Pharmacology, (2018), 94: 172-182.
Binson et al., "Preparation and Physicochemical Stability of Liquid Oral Dosage Forms Free of Potentially Harmful Excipient Designed for Pediatric Patients", Pharmaceutics (2019), 11(190): 11-13.
CAS Registry No. 58-94-6 for Chlorthiazide (CRZ) (2021).
CAS Registry No. 121-30-2 for Salamide (BTZ RC-A) (2021).
CAS Registry No. 5233-42-1 for 5-chloro-hydrochlorozide (5-CRZ) (2021).
CAS Registry No. 402824-96-8 for HCTZ Related Compound C (2021).
Cirri et al., "Development of a stable oral pediatric solution of hydrochlorothiazide by the combined use of cyclodextrins and hydrophilic polymers", International Journal of Pharmaceutics (2020) 587(25) 119692: 1-9.
Connors et al., Chemical Stability of Pharmaceuticals: A handbook for Pharmacists, 2nd Ed. (1986): 345-350 and 478-482.
Deppeler., "Hydrochlorothiazide", Analytical Profiles of Drug Substances (1981) 10: 405-440.
Desai et al., "Effects of different types of lactose and disintegrant on dissolution stability of hydrochlorothiazide capsule formulations", International Journal of Pharmaceutics (1994) 110(3): 257-265.
"Hydrochlorothiazide 0.5 mg/ml Oral Solution Product Description", European Paediatric Formulary (2019).
"Hydrochloric Acid, Dilute", European Pharmacopoeia 5.0: 1756-1757 (2015).
Tablet Package Insert, "Hydrochlorothiazide Tablets USP Prescribing Information", Teva Pharmaceuticals USA, Inc., (2020).
Jacob et al., "A toxicity assessment of 30 pharmaceuticals using Aliivibrio fischeri: a comparison of the acute effects of different formulations", Environmental Technology (2016) 37(21): 2760-2767.
Li, Y.Y., "Development of a Hydrochlorothiazide 0.5 mg/ml Oral Solution for Children", Eur J Hosp Pharm (2013) 20 (Suppl. 1): A71.
Mendes et al., "Physicochemical and microbiological stability studies of extemporaneous antihypertensive pediatric suspensions for hospital use", Pharmaceutical Development and Technology (2013) 18(4): 813-820.
Patel et al., "Bioavailability of Hydrochlorothiazide from Tablets and Suspensions", Journal of Pharmaceutical Sciences (1984) 73(3): 359-361.
Patel et al., "Development and evaluation of in situ novel intragastric controlled-release formulation of hydrochlorothiazide", Acta Pharma (2011) 61: 73-82.
Santoveña et al., "Design of a pediatric oral formulation with a low proportion of hydrochlorothiazide", International Journal of Pharmaceutics (2012) 423(2): 360-364.

(Continued)

*Primary Examiner* — John S Kenyon
(74) *Attorney, Agent, or Firm* — Merchant & Gould P.C.; Daniel R. Evans

(57) ABSTRACT

Disclosed herein is a powder for oral suspension and a reconstituted product thereof comprising highly pure hydrochlorothiazide, which is useful for treating hypertension and edema.

20 Claims, No Drawings

(56) References Cited

OTHER PUBLICATIONS

Shah et al., "In Vitro Release of Hydrochlorothiazide from Capsule Formulations", Drug Development and Industrial Pharmacy (1981) 7(6): 683-691.
Tagliari et al, "Evaluation of Physicochemical Characteristics of Suspensions Containing Hydrochlorothiazide Developed for Pediatric Use", Latin American Journal of Pharmacy (2009) 28(5): 734-740.
The United States Pharmacopeia, "Hydrochlorothiazide—USP 28", USP NF: 954-955 (2005).
Barbhaiya et al. Comparative bioavailability and pharmacokinetics of hydrochlorothiazide from oral tablet dosage forms, determined by plasma level and urinary excretion methods, Biopharmaceutics and Drug Disposition (1982) 3(4): 329-336.
Beermann et al., Pharmacokinetics of hydrochlorothiazide in man, European Journal of Clinical Pharmacology (1977) 12(4): 297-303.
Devineni et al., Effects of hydrochlorothiazide on the pharmacokinetics, pharmacodynamics, and tolerability of canagliflozin, a sodium glucose co-transporter 2 inhibitor, in healthy participants, Clinical Therapeutics (2014) 35(5): 698-710.
Niemeyer et al., Pharmacokinetics of hydrochlorothiazide in relation to renal function, European Journal of Clinical Pharmacology (1983) 24(5): 661-665.
Redalieu et al., Determination of plasma hydrochlorothiazide levels in humans, Journal of Pharmaceutical Sciences (1978) 67(5): 726-728.
Williams et al., Hydrochlorothiazide pharmacokinetics and pharmacologic effect: the influence of indomethacin, The Journal of Clinical Pharmacology (1982) 22(1): 32-41.

\* cited by examiner

HYDROCHLOROTHIAZIDE COMPOSITIONS

RELATED APPLICATIONS

This application is a continuation-in-part of U.S. patent application Ser. No. 17/546,175 filed on Dec. 9, 2021 which claims priority from Indian Patent Application No. 202041053842, filed on Dec. 10, 2020.

FIELD

The disclosure relates to a powder for oral suspension and a reconstituted product thereof comprising highly pure hydrochlorothiazide, which is useful for treating hypertension and edema.

BACKGROUND

Hydrochlorothiazide (or HCTZ) is chemically known as 6-Chloro-3,4-dihydro-2H-1,2,4-benzothiadiazine-7-sulfonamide-1,1-dioxide and may be represented chemically as follows:

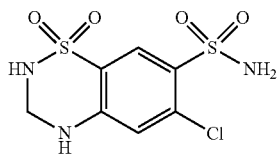 [SMILES: NS(=O)(=O)c1cc2c(cc1Cl)NCNS2(=O)=O]

HCTZ is a white, or practically white, crystalline powder and it is slightly soluble in water, but freely soluble in sodium hydroxide solution.

Hydrochlorothiazide is a thiazide diuretic. Thiazides affect the renal tubular mechanisms of electrolyte reabsorption, directly increasing excretion of sodium and chloride in approximately equivalent amounts. Indirectly, the diuretic action of hydrochlorothiazide reduces plasma volume, with consequent increases in plasma renin activity, increases in aldosterone secretion, increases in urinary potassium loss, and decreases in serum potassium. The renin-aldosterone link mediated by angiotensin, so co-administration of an ACE inhibitor tends to reverse the potassium loss associated with these diuretics. The mechanism of the antihypertensive effect of thiazides is unknown.

Novello relates generally to hydrochlorothiazide and its manufacture. Novello discloses HCTZ-containing compressed tablets.

Patel 1984 investigates bioavailability of Hydrodiuril (HCTZ) tablets and suspension dosage forms prepared from crushed Hydrodiuril tablets suspended in water. Patel 1984 does not address HCTZ stability of this suspension. And crushing tablets is not a safe practice due to the likelihood of contamination.

Ahn discloses a pharmaceutically acceptable solution of triamterene and hydrochlorothiazide, where hydrochlorothiazide is solubilized in a combination of a propylene glycol and polyethylene glycol 600 and the final pH is about 5. However, Ahn does not address HCTZ stability and no known formulation was approved by a regulatory authority based on Ahn's products.

In this regard, HCTZ may be sensitive to hydrolytic degradation to form salamide and formaldehyde. Connors at 479 and Deppler at 425-426. HCTZ degradation is undesirable not only because of the loss of active, but also because of the formation of formaldehyde, as formaldehyde is known to be a mutagen. Bercu at 176. As HCTZ may be administered to a patient for an extended period of time, it is desirable to limit the potential exposure to formaldehyde. In this regard, Jacob evaluated the environmental toxicity for reference and generic formulations of thirty drugs including hydrochlorothiazide tablet. Jacob suggested that the generic formulation of hydrochlorothiazide is toxic to the environment due to the excipients present in the generic tablet. Desai investigated HCTZ capsule dissolution and concluded that formaldehyde may interact negatively with an excipient resulting in reduced dissolution. And Shah investigated the dissolution profile of five HCTZ-containing hard gelatin capsule formulations stating among other things that the FDA recognized that HCTZ was known to exhibit potential bioavailability problems.

Hernandez discloses a hard gelatin capsule containing liquid pharmaceutical formulation including telmisartan and HCTZ and diethylene glycol monoethyl ether, among other things.

Patel 2011 discloses capsules (hard or soft gelatin) that includes HCTZ for an in situ forming intragastric formulation ("ISFIF").

As seen from the foregoing, a gelatin capsule may be problematic with respect to HCTZ because of sensitivity to moisture, temperature, and residual impurities present in other excipients and the pharmaceutically active ingredient. Moisture exchange rate between the gelatin shell and excipients plays a critical role in gelatin shell stability. The optimum water content for liquid filled masses is a necessary analysis, while the physico-mechanical and physicochemical properties of gelatin in the presence of heat, water, and stress. Another drawback of a gelatin capsule is that gelatin may not be compatible for all excipients particularly excipients containing an aldehyde group, a reducing sugar, ascorbic acids, peroxides. Therefore, a compatibility study of gelatin capsules and excipients used to formulate the ISFIFs is critical during the formulation development process.

Recently, efforts have been made to develop aqueous HCTZ-containing formulations. Cirri, Li, and the HCTZ (0.5 mg/mL) Product Information. As for the HCTZ (0.5 mg/mL) Product Information, the reported shelf life is 6 months (including in-use period) and the salamide limit is 6.0%, which exceeds the USP salamide limit of NMT 1.0%. A 6.0% salamide content may result in the formation of an unacceptable amount of formaldehyde. As a point of reference, salamide may be represented chemically as follows:

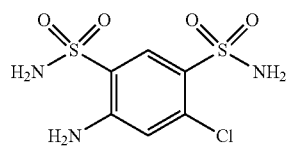

There are numerous reports related to extemporaneously prepared HCTZ preparations. See, e.g., Patel 1984; Binson, Santoveria, and Tagliari. However, none of these reports provide an HCTZ-containing formulation having maintenance of content uniformity, suspendability, and antimicrobial effectiveness for a suitable long-term.

There are many routes of treatment available for drug administration. Based on simplicity, oral administration of drugs is one of the preferred routes for treatment. As stated above, hydrochlorothiazide is also administered orally in the form of tablet or capsule for treating edema and high blood pressure. It is generally known that certain segments of the population have difficulty ingesting and swallowing solid oral dosage forms such as tablets and capsules particularly pediatrics and geriatrics, as well as hospitalized patients that may require a feeding tube.

Additionally, certain solid oral dosage forms of medications cannot be administered simply by crushing (e.g., patients requiring various types of feeding tubes) because of the coating or drug delivery mechanism. Many people in the total population have this difficulty which leads to non-compliance with the recommended medical therapy with the solid dosage forms, thereby resulting in rending the therapy ineffective.

Additionally, the dose of Hydrochlorothiazide to be given to the pediatric, geriatric and patients with feeding tubes are calculated according to the patient's weight. When the calculated dose is something other than the amount present in one or more intact solid dosage forms, the solid dosage form must be divided to provide the correct dose. This leads to the likelihood of inaccurate dosing when solid dosages forms, such as tablets and capsules are compounded to prepare other formulations for the aforementioned patients.

Otherwise, the compounding pharmacist breaks and crushes the hydrochlorothiazide tablets or capsules into a powder via mortar and pestle and reconstitute the powder in some liquid form. It is another method to overcoming use of tablet and capsule form to children, the geriatric and patients with feeding tubes. This method has significant drawbacks of including large variability in the actual dosage, rapid instability, and inconsistent formulation methods per compounding pharmacy, incomplete solubilizing of the Hydrochlorothiazide tablet or capsule in the liquid and several other potential issues. The liquid formulation obtained by crushing tablet or capsule may also be potentially unsafe due to contamination with residual drugs and other substances from the mortar and pestle or another crushing agent.

In view of the foregoing, there is a need for a safe, pharmaceutically elegant, and stable hydrochlorothiazide liquid compositions that are may be adapted for administration to certain patient populations that overcome the drawbacks with solid pharmaceutical compositions.

The present inventors surprisingly discovered a liquid composition for oral administration comprising hydrochlorothiazide having a low level of salamide and exhibits long-term stability with respect to hydrochlorothiazide content. The present dosage form liquid composition disclosed herein is safe and easy available for oral administration especially for geriatric population and hospitalized patients. The present stable liquid composition disclosed herein provides a better solution for aforementioned problems.

Objective

An objective disclosed herein relates to pharmaceutically acceptable oral liquid formulation of hydrochlorothiazide having a reduced salamide content for oral administration.

SUMMARY

Disclosed herein is a powder for oral suspension for oral administration, comprising about 3% w/w to about 5% w/w of hydrochlorothiazide; at least one thickening agent; and at least one pharmaceutically acceptable excipient; wherein the powder for oral suspension composition in 5 mL of water has a pH in the range of 3.5 to 5.5

DETAILED DESCRIPTION

The following paragraphs detail various embodiments of the invention. For the avoidance of doubt, it is specifically intended that any particular feature(s) described individually in any one of these paragraphs (or part thereof) may be combined with one or more other features described in one or more of the remaining paragraphs (or part thereof). In other words, it explicitly intended that the features described below individually in each paragraph (or part thereof) represent important aspects of the invention that may be taken in isolation and combined with other important aspects of the invention described elsewhere within this specification as a whole and including the examples and figures. The skilled person will appreciate that the invention extends to such combinations of features and that these have not been recited in detail here in the interests of brevity.

Definitions of some of the terms used herein to describe the invention are detailed below.

The use of the terms "a" and "an" and "the" and similar references in the context of describing the liquid composition described herein (especially in the context of the following claims) are to be construed to cover both the singular and the plural, unless otherwise indicated herein or clearly contradicted by context.

The term "about" is as used herein embodies standard error associated with a physicochemical observable to provide flexibility to a numerical range endpoint by providing that a given value may be "a little above" or "a little below" the endpoint. As used herein, the term "about" means a slight variation of the value specified, for example, preferably within 10% of the value specified. A stated amount for a compositional ingredient that is not preceded by the term "about" does not mean that there is no variance for the stated term, as one of ordinary skill would understand that there may be the possibility of a degree of variability generally associated with experimental error.

The term "therapeutically effective amount" or "effective dose" as used herein refers to the amount or dose of hydrochlorothiazide that is sufficient to initiate therapeutic response in a patient.

Pharmacodynamics of Hydrochlorothiazide

Acute antihypertensive effects of thiazides are thought to result from a reduction in blood volume and cardiac output, secondary to a natriuretic effect, although a direct vasodilatory mechanism has also been proposed. With chronic administration, plasma volume returns toward normal, but peripheral vascular resistance decreased. The exact mechanism of the antihypertensive effect of hydrochlorothiazide is unknown. Thiazides do not affect normal blood pressure. Onset of action occurs within 2 hours of dosing, peak effect observed at about 4 hours, and activity persists for up to 24 hours.

Pharmacokinetics of Capsule Dosage Form

Hydrochlorothiazide is well-absorbed (65% to 75%) following oral administration. Absorption of hydrochlorothiazide reduced in patients with congestive heart failure. Peak plasma concentrations observed within 1 to 5 hours of dosing and range from 70 to 490 ng/mL following oral doses of 12.5 mg to 100 mg. Plasma concentrations are linearly related to the administered dose. Concentrations of hydrochlorothiazide are 1.6 to 1.8 times higher in whole blood than in plasma. Binding to serum proteins has reported to be approximately 40% to 68%. The plasma elimination half-life has reported to be 6 to 15 hours. Hydrochlorothiazide eliminated primarily by renal pathways. Following oral doses of 12.5 mg to 100 mg, 55% to 77% of the administered dose appears in urine and greater than 95% of the absorbed dose excreted in urine as unchanged drug. In patients with renal disease, hydrochlorothiazide plasma concentrations may be increased and the elimination half-life may be prolonged. When hydrochlorothiazide capsules administered with food, its bioavailability is reduced by 10%, the maximum plasma concentration is reduced by 20%, and the time to maximum concentration increases from 1.6 to 2.9 hours.

Development activities reported herein resulted in the discovery of a hydrochlorothiazide-containing oral powder for suspension formulation exhibiting a salamide content of less than 1.0% for at least six-months when stored under ambient conditions.

Liquid Formulation:

One embodiment relates to a liquid composition for oral administration, comprising: about 10 mg to about 50 mg in 3-10 mL hydrochlorothiazide; at least one solubilizer; at least one pH modifier; and at least one pharmaceutically acceptable excipients; wherein the pH of oral liquid composition is about 3.5 to about 5.5.

In yet another embodiment, at least one solubilizer is selected from Cremophor RH 40, Cremophor EL, Poloxamer 188 and PEG 6000 and combination thereof.

In yet another embodiment, the liquid composition comprises, at least one pharmaceutically acceptable excipient selected from a vehicle, a preservative, and a sweetener.

In another embodiment the vehicle used in the oral liquid formulation is selected from glycerin, a C2 to C8 mono- and poly-alcohol (e.g., ethanol), a C7 to C18 alcohol of linear or branched configuration, water and mixtures thereof; including, for example, ethanol, glycerin, propylene glycol, water, or a mixture thereof.

In one aspect, the oral liquid formulation comprises a vehicle in an amount of from about 10% w/v to about 30% w/v. In one aspect, the liquid oral formulation comprises hydrochlorothiazide and a solubilizer dissolved in the vehicle.

In another aspect, the oral liquid formulation is substantially free of water, including, for example, an amount of water less than about 20% w/v, about 19% w/v, about 18% w/v, about 17% w/v, about 16% w/v, about 15% w/v, about 14% w/v, about 13% w/v, about 12% w/v, about 11% w/v, about 10% w/v, about 9% w/v, about 8% w/v, about 7% w/v, about 6% w/v, about 5% w/v, about 4% w/v, about 3% w/v, about 2% w/v, about 1% w/v, about 0.5% w/v, and about 0.1% w/v.

In another aspect, the oral liquid formulation comprises a preservative selected from the group consisting of sodium benzoate, benzoic acid, potassium sorbate, paraben, methylparaben, ethylparaben, propylparaben, butylparaben, isobutylparaben, benzyl alcohol, boric acid, calcium acetate, bentonite, cetrimide, chlorhexidine, cetylpyridinium chloride, cresol, chlorbutanol, magnesium trisilicate, and a combination thereof.

In another aspect, the oral liquid formulation comprises a preservative in an amount of about 0.5 mg/mL to 4 mg/mL.

Powder for Oral Suspension

Disclosed herein is a powder for oral suspension composition for oral administration comprising: about 3% w/w to about 5% w/w hydrochlorothiazide; a thickening agent; and at least one pharmaceutically acceptable excipient; wherein the powder for oral suspension composition in 5 mL of water has a pH of from about 3.5 to about 5.5.

In one aspect, the powder comprises about 3% w/w to about 5% w/w hydrochlorothiazide and all values in between, including, for example about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4.0% w/w, about 4.1% w/w, about 4.2% w/w, about 4.3% w/w, about 4.4% w/w, about 4.5% w/w, about 4.6% w/w, about 4.7% w/w, about 4.8% w/w, and about 4.9% w/w. In another aspect, for example, the powder comprises of from about 3.2% w/w to about 4.2% w/w of hydrochlorothiazide.

In yet another aspect, the powder has a water content of not more than about 0.8% w/w. In a further aspect, the powder has a water content ranging from about 0.1% w/w to about 0.8% w/w and all values in between, including, for example 0.2% w/w, 0.3% w/w, 0.4% w/w, 0.5% w/w, 0.6% w/w, and 0.7% w/w.

In one aspect, the powder comprises at least one thickening agent selected from hydrocolloid gum, cellulosic derivative, a polysaccharide, alginate, acrylic acid copolymer, polyvinylpyrrolidone, aluminium magnesium silicate, and a combination thereof. Examples of at least thickening agent includes, but is not limited to, a guar gum, a locust bean gum, gum karaya, gum tragacanth, gum Arabic, and xanthan gum.

In another aspect, the powder comprises at least one thickening agent in an amount of from about 0.4% w/w to about 5% w/w. In one aspect, the powder comprises at least one thickening agent comprising a gum in an amount of from about 0.4% w/w to about 5% w/w, wherein the gum comprises a guar gum, a locust bean gum, gum karaya, gum tragacanth, gum Arabic, xanthan gum, or a combination thereof. In yet another aspect, the powder comprises at least one thickening agent comprising xanthan gum in an amount of from about 0.4% w/w to about 5% w/w. In a further aspect, the powder comprises at least one thickening agent comprising xanthan gum in an amount of from about 0.4% w/w to about 2.5% w/w and all values in between, including, for example, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, 1.9% w/w, about 2.0% w/w, about 2.1% w/w, about 2.2% w/w, about 2.3% w/w and about 2.4% w/w. In yet another aspect, the powder comprises at least one thickening agent comprising xanthan gum in an amount of from about 0.8% w/w to about 2.0% w/w. In a further aspect, the powder comprises at least one thickening agent comprising xanthan gum in an amount of from about 1.1% w/w to about 2.0% w/w.

In one aspect, the at least one pharmaceutically acceptable excipient comprises a preservative and a sweetener.

In one aspect, the at least one pharmaceutically acceptable excipient comprises a preservative selected from the group consisting of sodium benzoate, benzoic acid, potassium sorbate, paraben, methylparaben, ethylparaben, propylparaben, butylparaben, isobutylparaben, benzyl alcohol, boric acid, calcium acetate, bentonite, cetrimide, chlorhexidine, cetylpyridinium chloride, cresol, chlorbutanol, magnesium trisilicate, and a combination thereof.

In one aspect, the at least one pharmaceutically acceptable excipient comprises a preservative selected from the group consisting of sodium benzoate, benzoic acid, potassium sorbate, paraben, methylparaben, ethylparaben, propylparaben, butylparaben, isobutylparaben, benzyl alcohol, boric acid, calcium acetate, bentonite, cetrimide, chlorhexidine, cetylpyridinium chloride, cresol, chlorbutanol, magnesium trisilicate, and a combination thereof in an amount of from about 0.01% w/w to about 5% w/w and all values in between, including, for example, about 0.1% w/w, about 0.2% w/w, about 0.3% w/w, about 0.4% w/w, about 0.5% w/w, about 0.6% w/w, about 0.7% w/w, about 0.8% w/w, about 0.9% w/w, about 1.0% w/w, about 1.1% w/w, about 1.2% w/w, about 1.3% w/w, about 1.4% w/w, about 1.5% w/w, about 1.6% w/w, about 1.7% w/w, about 1.8% w/w, about 1.9% w/w, about 2.0% w/w, about 2.1% w/w, about 2.2% w/w, about 2.3% w/w, about 2.4% w/w, about 2.5% w/w, about 2.6% w/w, about 2.7% w/w, about 2.8% w/w, about 2.9% w/w, about 3.0% w/w, about 3.1% w/w, about 3.2% w/w, about 3.3% w/w, about 3.4% w/w, about 3.5% w/w, about 3.6% w/w, about 3.7% w/w, about 3.8% w/w, about 3.9% w/w, about 4.0% w/w, about 4.1% w/w, about 4.2% w/w, about 4.3% w/w, about 4.4% w/w, about 4.5% w/w, about 4.6% w/w, about 4.7% w/w, about 4.8% w/w, and about 4.9% w/w.

In another aspect, the at least one pharmaceutically acceptable excipient comprises a preservative selected from the group consisting of sodium benzoate, benzoic acid, potassium sorbate, paraben, methylparaben, ethylparaben, propylparaben, butylparaben, isobutylparaben, benzyl alcohol, boric acid, calcium acetate, bentonite, cetrimide, chlorhexidine, cetylpyridinium chloride, cresol, chlorbutanol, magnesium trisilicate, and a combination thereof in an amount of from about 0.1% w/w to about 2.0% w/w and all values in between, including, for example, about 0.2% w/w, about 0.3% w/w, about 0.4% w/w, about 0.5% w/w, about 0.6% w/w, about w/w, about 0.8% w/w, about 0.9% w/w, about 1.0% w/w, 1.1% w/w about 1.2% w/w, about 1.3% w/w, about 1.4% w/w, about 1.5% w/w, about 1.6% w/w, about 1.7% w/w, about 1.8% w/w and about 1.9% w/w.

In one aspect of the powder disclosed herein, the at least one pharmaceutically acceptable excipient comprises a sweetener selected from the group consisting of sucralose, maltilol, liquid glucose, magnasweet 110, magnasweet 180, saccharin sodium, xylitol, sorbitan monoleate, sorbitol, sucrose, aspartame, acesulfame potassium, and a combination thereof.

In one aspect of the powder disclosed therein, the at least one pharmaceutically acceptable excipient comprises a sweetener selected from the group consisting of sucralose, maltilol, liquid glucose, magnasweet 110, magnasweet 180, saccharin sodium, xylitol, sorbitan monoleate, sorbitol, sucrose, aspartame, acesulfame potassium, and a combination thereof in an amount of from about 0.1% w/w to about 96% w/w.

In one aspect of the powder disclosed herein, the at least one pharmaceutically acceptable excipient comprises a sweetener selected from the group consisting of sucralose, sucrose, and a combination thereof in an amount of from about 90% w/w to about 96% w/w, and all values in between, including, for example about 91% w/w, about 92% w/w, about 93% w/w, about 94% w/w, and about 95% w/w.

In another aspect of the powder disclosed herein, the at least one pharmaceutically acceptable excipient comprises a pH modifier selected from group consisting of citric acid, fumaric acid, tartaric acid, malic acid, sodium phosphate monobasic, potassium phosphate, maleic acid, lactic acid, hydrochloric acid, phosphoric acid, and a combination thereof.

In yet another aspect of the powder disclosed herein, the at least one pharmaceutically acceptable excipient comprises a pH modifier selected from group consisting of citric acid, fumaric acid, tartaric acid, malic acid, sodium phosphate monobasic, potassium phosphate, maleic acid, lactic acid, hydrochloric acid, phosphoric acid, and a combination thereof in an amount of from about 0.2% w/w to about 1.2% w/w and all values in between, including, for example about 0.3% w/w, about 0.4% w/w, about 0.5% w/w, about 0.6% w/w, about 0.7% w/w, about 0.8% w/w, about 0.9% w/w, about 1.0% w/w, and about 1.1% w/w.

In one aspect, the powder disclosed herein has a salamide impurity content of not more than 1.0% for at least about 6-months when stored at 25±2° C. and 60±5% relative humidity and 40° C. and 75% relative humidity.

One aspect relates to a bottle comprising 5 to 50 doses of the powder for oral suspension for oral administration and all values in between, including for example, 5 doses, 10 doses, 15 doses, 20 doses, 25, doses, 30 doses, 35 doses, 40 doses, and 45 doses. In one aspect, a dose may comprise 50 mg of hydrochlorothiazide. Another aspect relates to kit comprising a bottle comprising the powder for oral suspension, as disclosed herein, and written instructions for reconstitution of the powder as an oral liquid suspension comprising HCTZ in an amount of about 50 mg/5 mL, as well as instructions for administration of the oral liquid suspension.

One aspect relates to an oral liquid suspension comprising the powder for oral suspension and a pharmaceutically acceptable carrier comprising water.

Another aspect relates to an oral liquid suspension comprising the powder for oral suspension and a pharmaceutically acceptable carrier comprising water comprising about 40 mg/5 mL to about 60 mg/5 mL of hydrochlorothiazide.

Another aspect relates to an oral liquid suspension comprising the powder for oral suspension and a pharmaceutically acceptable carrier comprising water and comprising about 50 mg/5 mL of hydrochlorothiazide.

Another aspect relates to an oral liquid suspension comprising the powder for oral suspension and a pharmaceutically acceptable carrier comprising water and a thickening agent comprising xanthan gum in an amount of from about 5 mg/5 mL to about 20 mg/5 mL.

Another aspect relates to an oral liquid suspension comprising the powder for oral suspension and a pharmaceutically acceptable carrier comprising water, wherein the reconstituted product has a pH of about 3.5 to about 5.5, and all values in between, including for example, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, and about 5.4.

In one aspect, an oral liquid suspension comprising the powder for oral suspension and a pharmaceutically acceptable carrier comprising water has a viscosity of from about 70 cP to about 120 cP, and all values in between, including, for example, about 80 cP, about 90 cP, about 100 cP, and about 110 cP.

Another aspect relates to an oral liquid suspension comprising the powder for oral suspension and a pharmaceutically acceptable carrier comprising water, wherein the hydrochlorothiazide concentration is about 50 mg/5 mL (or HCTZ≈10 mg/mL), and wherein the oral liquid suspension has a salamide impurity content not more than 1.0% for at least about 6-months when stored at 25±2° C. and 60±5% relative humidity after reconstitution.

One aspect disclosed herein relates to a method of treating edema and hypertension comprising administering to a patient in need thereof a therapeutically effective amount of the oral liquid suspension disclosed herein.

Another aspect disclosed herein relates to a method of treating edema and hypertension comprising administering to a human patient in need thereof a therapeutically effective amount of the oral liquid suspension disclosed herein, wherein said administration of the oral liquid suspension to the human patient provides a geometric least squares mean for $C_{max}$ of from about 200 ng/mL to about 450 ng/mL, a geometric least squares mean for $AUC_{0-\infty}$ of from about 1800 ng•hr/mL to about 2900 ng•hr/mL, or a combination thereof.

A geometric least squares mean for $C_{max}$ of from about 200 ng/mL to about 450 ng/mL includes, for example, all values in between, such as about 220 ng/mL, about 240 ng/mL, about 260 ng/mL, about 280 ng/mL, about 300 ng/mL, about 320 ng/mL, about 340 ng/mL, about 360 ng/mL, about 380 ng/mL, about 400 ng/mL, about 420 ng/mL, and about 440 ng/mL. For instance, one aspect relates to geometric least squares mean for $C_{max}$ of from about 300 ng/mL to about 400 ng/mL.

A geometric least squares mean for $AUC_{0-\infty}$ of from about 1800 ng•hr/mL to about 2900 ng•hr/mL includes, for example, all values in between, such as about 2000 ng•hr/mL, about 2100 ng•hr/mL, about 2200 ng•hr/mL, about 2300 ng•hr/mL, about 2400 ng•hr/mL, about 2500 ng•hr/mL, about 2600 ng•hr/mL, about 2700 ng•hr/mL, and about 2800 ng•hr/mL. For instance, one aspect relates to geometric least squares mean for $AUC_{0-\infty}$ of from about 2300 ng•ng/mL to about 2600 ng•ng/mL.

Another aspect disclosed herein relates to a method of treating edema and hypertension comprising administering to a human patient in need thereof a therapeutically effective amount of the oral liquid suspension disclosed herein, wherein said administration of the oral liquid suspension to the human patient provides a geometric least squares mean for $C_{max}$ of about 318 ng/mL, a geometric least squares mean for $AUC_{0-\infty}$ of about 2300 ng•hr/mL, or a combination thereof.

Yet, another aspect disclosed herein relates to a method of treating edema and hypertension comprising administering to a human patient in need thereof a therapeutically effective amount of the oral liquid suspension disclosed herein, wherein said administration of the oral liquid suspension to the human patient results in a geometric least squares mean for $C_{max}$ of about 314 ng/mL, a geometric least squares mean for $AUC_{0-\infty}$ of about 2350 ng•hr/mL, or a combination thereof.

Yet, another aspect disclosed herein relates to a method of treating edema and hypertension comprising administering to a human patient in need thereof a therapeutically effective amount of the oral liquid suspension disclosed herein, wherein said administration of the oral liquid suspension to the human patient results in a geometric least squares mean for $C_{max}$ of about 382 ng/mL, a geometric least squares mean for $AUC_{0-\infty}$ of about 2544 ng•hr/mL, or a combination thereof.

Another aspect relates to a pharmaceutical composition comprising a means for providing a geometric least squares mean for $C_{max}$ of from about 200 ng/mL to about 450 ng/mL, a geometric least squares mean for $AUC_{0-\infty}$ of from about 1800 ng•hr/mL to about 2900 ng•hr/mL, or a combination thereof, In yet another aspect, the means comprises administering to a human a therapeutically effective amount of an oral liquid suspension based on any one of the powder for oral suspensions disclosed herein.

Another aspect relates to a pharmaceutical composition comprising a means for providing a geometric least squares mean for $C_{max}$ of from about 200 ng/mL to about 450 ng/mL, a geometric least squares mean for $AUC_{0-\infty}$ of from about 1800 ng•hr/mL to about 2900 ng•hr/mL, or a combination thereof, In yet another aspect, the means comprises administering to a human a therapeutically effective amount of an oral liquid suspension based on any one of the powder for oral suspensions disclosed herein.

Another aspect disclosed herein relates to a method of treating edema and hypertension comprising administering to a human patient in need thereof a therapeutically effective amount of the oral liquid suspension disclosed herein, wherein said administration of the oral liquid suspension to the human patient provides a geometric least squares mean for $C_{max}$ of about 305 ng/mL, a geometric least squares mean for $AUC_{0-\infty}$ of about 2265 ng•hr/mL, or a combination thereof.

The information that follows identifies exemplified embodiments of the oral liquid formulation disclosed herein and is not meant to be limiting.

Unless specified herein, studies and/or observables reported herein correspond to monographs according to the USP, including for example, dissolution (USP<711>), pH (USP<791>), and viscosity (USP<912>, Method III, using cone and plate method by Brookfield DV-1 viscometer, Spindle CP52, RPM 60 at 25° C.±0.1° C.).

Example 1

Oral liquid formulations (1A, 1B, and 1C) comprise HCTZ in an amount of about 50 mg/5 mL different ratio of solvents is presented in below table 1.

TABLE 1

Makeup of Formulation numbers 1A, 1B, and 1C

| Ingredient | Formulation No. | | |
| --- | --- | --- | --- |
| | 1A g/10 mL | 1B g/10 mL | 1C g/10 mL |
| Hydrochlorothiazide | 0.10 | 0.10 | 0.10 |
| Ethanol | 2.50 | 2.50 | 2.00 |
| Propylene glycol | 2.50 | 2.50 | 5.00 |
| Glycerin | 0.60 | 2.50 | 1.00 |
| Sodium Benzoate | 0.01 | 0.01 | 0.02 |
| Sucralose | 0.01 | 0.01 | 0.02 |
| Citric acid anhydrous | 0.045 | 0.055 | 0.115 |
| Purified water | qs to 10 mL | qs to 10 mL | qs to 10 mL |
| pH | 3.54 | 3.59 | 3.58 |

Manufacturing Process:

A 2 L batch was manufactured as follows, to a mixture of ethanol and propylene glycol; hydrochlorothiazide was added and stirred continuously. To this mixture glycerin was added under stirring followed by water was added. To the above mixture citric acid, Sucralose and sodium benzoate was added and stirred until clear solution was obtained. The volume of the mixture was adjusted to 2 L with purified water. A prepared 1.7 oz (50 mL) solution was packed in 2.03 oz of white high density polyethylene bottles with 33 mm child resistance closure and stored inverted under various stability conditions (e.g., Accelerated (40° C./75% relative humidity ("RH")), Ambient (25° C./60% RH), and Refrigerated (2-8° C.).

Stored samples were analyzed for appearance and pH. pH-values were measured in a manner consistent with USP<791>.

Stored samples also were analyzed for assay (% w/w). The reported amount of hydrochlorothiazide (expressed as Assay (% w/w)) was determined by HPLC with reference to a suitable calibration curve using hydrochlorothiazide USP as reference standard.

Further, stored samples were analyzed for impurities and related substances. (viz., Salamide (Benzothiadiazine related compound A ("BTZ RC-A" CAS Registry No. 121-30-2), chlorthiazide ("CRZ" CAS Registry No. 58-94-

6); 5-Chlorothiazide ("5-CRZ" CAS Registry No. 5233-42-1); Hydrochlorothiazide impurity C (HCTZ IMP C" CAS Registry No. 402824-96-8) were evaluated by HPLC. Amounts of impurities and related substances were determined by HPLC, as described in, for example, USP 40-NF35 hydrochlorothiazide Monograph; see also USP 2005; and EP 5.0.

Amounts of impurities and related substances were determined by HPLC, as described in, for example, USP 40-NF35 hydrochlorothiazide monograph.

Table 2 includes the stability results for Formulations 1A, 1B, and 1C.

TABLE 2

Stability Data for Formulation 1A-1C
Related Substance (% w/w)

| FN | Condition | pH | Assay | BTZRC-A | CRZ | 5-CRZ | HCTZ IMP C | HU | TI |
|---|---|---|---|---|---|---|---|---|---|
| Limit(s): NMT | (w/w %) | | (% w/w) | 1.0 | 0.5 | 0.5 | 0.5 | 0.2 | 1.5 |
| 1A | Initial | 3.54 | 103.3 | 0.143 | 0.019 | 0.004 | 0.034 | 0.036 | 0.261 |
| | Accel., 3 M | 3.56 | 95.6 | 3.899 | 0.018 | 0.021 | 0.049 | 0.249 | 4.300 |
| | Ambient, 3 M | 3.49 | 95.8 | 0.192 | 0.017 | ND | 0.012 | 0.025 | 0.546 |
| | Refrig., 3 M | — | 97.7 | 0.720 | 0.020 | ND | ND | 0.051 | 0.791 |
| 1B | Initial | 3.59 | 104.8 | 0.123 | 0.018 | ND | 0.061 | 0.042 | 0.25 |
| | Accel., 3 M | 3.53 | 100.9 | 2.283 | 0.016 | ND | 0.026 | 0.144 | 2.492 |
| | Ambient, 3 M | 3.43 | 100.9 | 0.319 | 0.024 | ND | 0.008 | 0.022 | 0.373 |
| | Refrig., 3 M | — | 102.5 | 0.140 | 0.03 | 0.014 | 0.088 | ND | 0.272 |
| 1C | Initial | 3.58 | 100.6 | 0.178 | 0.027 | 0.008 | 0.091 | 0.174 | 0.505 |
| | Accel., 3 M | 3.77 | 97.5 | 1.566 | 0.014 | 0.016 | 0.013 | 0.109 | 1.718 |
| | Ambient, 3 M | 3.61 | 96.9 | 0.239 | 0.026 | ND | 0.009 | 0.023 | 0.297 |
| | Refrig., 3 M | — | 98.5 | 0.141 | 0.021 | ND | 0.077 | 0.019 | 0.258 |

Abbreviations/Key: FN: Formulation Number, NMT: not more than, Accel. (accelerated (40° C./75% RH)), Ambient (25° C./60% RH), Refrig. (refrigerated, 2-8° C), 3 M (3-months).

Based on the Table 2 data, it is evident that there is proportional increase in Salamide impurity under accelerated (40° C./75% RH) and long and 25° C./60% RH with increasing amounts of water (e.g., 1A (39% water), 1B (24% water), and 1C (19% water)). Formulations 1A (39% water) and 1B (24% water) resulted in HCTZ precipitation and/or HCTZ crystallization. The results suggest that minimizing/removing water from the composition resulted in a reduced amount of hydrolytic degradation (i.e., salamide formation). Further, a reduced water content prevented HCTZ crystallization.

Use of a solubilizer e.g., Cremophor RH 40, Cremophor EL, Poloxamer 188, and PEG solid grades) were investigated. Based on results presented herein, Cremophor RH40 and PEG 6000 showed marked increase in solubility of hydrochlorothiazide and concomitant inhibition of HCTC crystallization.

Example 2: Batch with Solubilizer

Hydrochlorothiazide oral solution prototype composition containing Cremophor RH40 and PEG 6000 is presented in table 3.

TABLE 3

Makeup of Formulation numbers 2A and 2B

| | Formulation No. | |
|---|---|---|
| | 2A | 2B |
| Ingredient | g/10 mL | g/5 mL |
| Hydrochlorothiazide | 0.10 | 0.10 |
| Ethanol | 2.00 | 1.00 |
| Propylene glycol | 4.00 | 3.00 |
| Glycerin | 2.00 | 0.90 |
| Sodium Benzoate | 0.02 | NA |
| Sucralose | 0.02 | 0.02 |
| Citric acid anhydrous | 0.19 | 0.025 |
| Cremophor RH40 | 0.50 | NA |
| PEG 6000 | NA | 0.04 |
| Water | Qs to 10 mL | Qs to 5 mL |

Brief Manufacturing Procedure

Formulation 2A

A 1 L batch was manufactured as follows, to a mixture of ethanol, propylene glycol and hydrochlorothiazide was added and stirred continuously. To this mixture glycerin was added under stirring followed by Cremophor RH40 was added. Sucralose and sodium benzoate dissolved in purified water and the solution added to the above mixture. To the above mixture, citric acid was added and the mixture stirred to obtain clear solution. The volume of the mixture was adjusted to 1 L with water. A prepared 1.7 oz (50 mL) solution was packed in 2.03 oz of white high density polyethylene bottles with 33 mm child resistance closure and stored inverted under various stability conditions.

Formulation 2B

A 2L batch was manufactured as follows, PEG 6000 dissolved in water by gentle warming. To the above solution, hydrochlorothiazide was added and stirred continuously. To this mixture Glycerin, Sucralose and Citric acid anhydrous was added to the above solution and mixed until clear solution is obtained and the volume is adjusted to 2 L with water. A prepared 1.7 oz (50 mL) solution was packed in 2.03 oz of white high density polyethylene bottles with 33 mm child resistance closure and stored inverted under various stability conditions.

TABLE 4

Stability Data for Formulation Nos. 2A and 2B
Related Substance (% w/w)

| FN | Condition | pH | Assay (% w/w) | BTZ RC-A | CRZ | 5-CRZ | HCTZ IMP C | HU | TI |
|---|---|---|---|---|---|---|---|---|---|
| | Limit(s): NMT | | (w/w %) | 1.0 | 0.5 | 0.5 | 0.5 | 0.2 | 1.5 |
| 2A | Initial | 3.59 | 101.5 | 0.195 | 0.020 | ND | 0.017 | 0.029 | 0.266 |
| | 40° C./75% 3 M | 3.50 | 99.0 | 1.032 | 0.017 | ND | 0.007 | 0.064 | 1.12 |
| | 25° C./60% 3 M | 3.39 | 98.9 | 0.214 | 0.020 | ND | 0.011 | 0.022 | 0.267 |
| | 2-8° C. 3 M | — | 100.4 | 0.150 | 0.021 | ND | 0.081 | ND | 0.252 |
| 2B | Initial | 3.0 | — | 0.075 | 0.025 | 0.004 | 0.018 | 0.028 | 0.15 |
| | 40° C./75% 1 M | — | — | 0.197 | 0.014 | ND | ND | 0.020 | 0.231 |

Abbreviations: FN: Formulation Number, NMT: not more than, Accel. (accelerated (40° C./75% RH)), LT (long-term (25° C./60% RH)), Refrig. (refrigerated, 2-8° C.), 3 M (3-months).

Based on the stability data, it is evident that there is increase in salamide under accelerated storage (40° C./75% RH) due to the presence of water. Hence, the data suggested that reduction of water content may result in reduced HCTZ degradative hydrolysis. Further, reduced water content may prevent HCTZ crystallization since the batch with PEG 6000 was found to be hazy under refrigerated (2-8° C.) storage.

Example 3: Batches without Water

Table 5 describes the composition of hydrochlorothiazide oral solution (50 mg/3.5 mL) without water. The pH was adjusted to 3 using 0.1N HCl and solution with as such pH is presented in below table 5.

TABLE 5

Makeup of Formulations 3A, 3B, and 3C

| | Formulation No | | |
|---|---|---|---|
| Ingredient | 3A g/7 mL | 3B g/7 mL | 3C g/7 mL |
| Hydrochlorothiazide | 0.10 | 0.10 | 0.10 |
| Ethanol | 1.58 | 1.58 | 1.58 |
| Propylene glycol | 5.18 | 4.00 | 5.18 |
| Glycerin | NA | 1.44 | NA |
| Sucralose | 0.02 | 0.02 | 0.02 |
| 0.1N HCl | — | — | qs to adjust pH |
| pH | 6.8 | 6.7 | 2.9 |

Brief Manufacturing Procedure:

A 0.5 L batch was manufactured as follows, to a propylene glycol, hydrochlorothiazide was added under stirring and stirred continuously. To the above solution, ethanol added under stirring followed by addition of sucralose and mixture stirred until clear solution obtained. A prepared 1.7 oz (50 mL) suspension was packed in 2.03 oz of white high density polyethylene bottles with 33 mm child resistance closure and stored inverted under various stability conditions.

TABLE 6

Stability Data for Formulations 3A, 3B, and 3C

| FN | Condition | pH | Assay (% w/w) | BTZ RC-A | CRZ | 5-CRZ | HCTZ IMP C | HU | TI |
|---|---|---|---|---|---|---|---|---|---|
| | Limit: NMT | | (% w/w) | 1.0 | 0.5 | 0.5 | 0.5 | 0.2 | 1.5 |
| 3C | Initial | 6.80 | 100.4 | 0.28 | 0.022 | 0.009 | 0.073 | 0.009 | 0.393 |
| | Accel., 3 M | 6.12 | 97.0 | 0.272 | 0.044 | ND | 0.207 | ND | 0.523 |
| | Ambient, 3 M | 6.22 | 97.4 | 0.308 | 0.018 | ND | 0.082 | ND | 0.408 |
| | Refrig., 3 M | — | 99.0 | 0.243 | 0.016 | ND | 0.091 | ND | 0.35 |
| 3B | Initial | 6.7 | 100.9 | 0.359 | 0.022 | ND | 0.07 | 0.004 | 0.455 |
| | Accel., 3 M | 5.97 | 98.8 | 1.043 | 0.032 | ND | 0.177 | 0.04 | 1.292 |
| | Ambient, 3 M | 6.01 | 99.7 | 0.484 | 0.026 | ND | 0.081 | 0.087 | 0.689 |
| | Refrig., 3 M | — | 99.0 | 0.026 | 0.055 | 0.089 | ND | 1.05 | 0.88 |
| 3A | Initial | 2.90 | 100.5 | 0.412 | 0.021 | 0.012 | 0.063 | 0.004 | 0.512 |
| | Accel., 3 M | 5.14 | 98.4 | 1.548 | ND | ND | 0.139 | 0.12 | 1.807 |
| | Ambient, 3 M | 4.58 | 96.3 | 0.438 | 0.022 | ND | 0.069 | ND | 0.529 |
| | Refrig., 3 M | — | 98.3 | 0.277 | 0.02 | ND | 0.089 | ND | 0.386 |

Abbreviations/Key: FN: Formulation Number, NMT: not more than, ND: not detected, Accel. (accelerated (40° C./75% RH)), Ambient (25° C./60% RH), Refrig. (refrigerated, 2-8° C.), 3M (3-months).

Based on the available stability data it is evident that, the formation of salamide in above formulation under accelerated (40° C./75% RH) and ambient (25° C./60% RH) without water is lower than formulation batches with water. The present inventors also found that the pH is important factor in the present formulation. Based on the above stability results, it is confirmed that oral liquid formulation with pH in the range of 2.5 to 3.5 is stable and there is no substantial change in impurity profile particularly in case of salamide and whereas in the batches with higher pH they have observed substantial increase of impurity profile particularly in accelerated conditions. Hence it is evident that water and pH has an effect the present oral liquid formulation.

The present oral liquid formulation of hydrochlorothiazide with lower level of impurity degradation particularly salamide is useful for treating hypertension and for the treatment of edema.

Batches with Suspension Approach

Example 4

As a first attempt Hydrochlorothiazide oral suspension 50 mg/5 mL formulation composition were developed to study the stability at different storage conditions. Examples are as presented in below Table 7.

TABLE 7

Makeup for Formulations 4A, 4B, and 4C

| Ingredient | 4A mg/5 mL | 4B mg/5 mL | 4C mg/5 mL |
|---|---|---|---|
| Hydrochlorothiazide | 50.0 | 50.0 | 50.0 |
| Sorbic acid | 2.5 | 2.5 | 2.5 |
| Xanthan gum | 12.5 | 12.5 | 12.5 |
| Sucralose | 2.5 | 2.5 | 2.5 |
| Simethicone emulsion | 10.0 | — | 10.0 |
| Poloxamer p188 | — | — | 2.5 |
| Cremophor RH40 | — | 5.0 | — |
| Glycerin | 250.0 | 250.0 | 250.0 |
| Citric acid anhydrous | qs to adjust pH | qs to adjust pH | qs to adjust pH |
| Purified water | qs | qs | qs |
| pH | 3.50 | 3.54 | 3.53 |

Brief Manufacturing Procedure:

Purified water was heated to 80° C. to dissolve sorbic acid and stirred. Xanthan gum was added, stirred vigorously and sucralose was added to it. Hydrochlorothiazide was dispersed in glycerin and water and added into above mixture. Cremophor RH40/Poloxamer p188 were added in respective batches. Citric acid (10% solution) was added to obtain the pH to 3.5 and the volume is made up with water to 1 L for example 4A and 2 L for example 4B, and example 4C. A prepared 1.7 oz (50 mL) solution was packed in 2.03 oz of white high density polyethylene bottles with 33 mm child resistance closure and stored inverted under various stability conditions.

TABLE 8

Stability Data for Formulations 4A, 4B, and 4C
Related Substance (% w/w)

| FN | Condition | pH | Assay (% w/w) Limit: NMT % | BTZ RC-A 1.0 | CRZ 0.5 | 5-CRZ 0.5 | HCTZ IMP C 0.5 | HU 0.2 | TI 1.5 |
|---|---|---|---|---|---|---|---|---|---|
| 4A | Initial | 3.50 | 97.8 | 0.204 | 0.019 | 0.006 | 0.081 | ND | 0.310 |
|  | Accel., 3 M | 3.46 | 96.7 | 1.686 | 0.043 | ND | 0.08 | 0.093 | 1.902 |
|  | Ambient, 3 M | 3.49 | 96.3 | 0.465 | 0.011 | ND | 0.084 | 0.028 | 0.588 |
| 4B | Initial | 3.54 | 104.5 | 0.35 | 0.02 | ND | 0.086 | 0.005 | 0.461 |
|  | Accel., 3 M | 3.43 | 70 | 1.724 | 0.051 | 0.007 | 0.089 | 0.139 | 2.010 |
|  | Ambient, 3 M | 3.5 | 103.4 | 0.408 | 0.02 | ND | 0.094 | 0.013 | 0.535 |
|  | Refrig., 3 M | — | 100.7 | 0.155 | 0.02 | ND | 0.107 | 0.034 | 0.316 |
| 4C | Initial | 3.53 | 104.0 | 0.351 | 0.02 | ND | 0.093 | ND | 0.464 |
|  | Accel., 3 M | 3.43 | 97.4 | 1.825 | 0..029 | ND | 0.101 | 0.102 | 2.028 |
|  | Ambient, 3 M | 3.53 | 98.0 | 0.429 | 0.016 | ND | 0.088 | ND | 0.533 |
|  | Refrig., 3 M | — | 100.8 | 0.230 | 0.018 | ND | 0.09 | ND | 0.338 |

Abbreviations/Key: FN: Formulation Number, NMT: not more than, ND: not detected, Accel. (accelerated (40° C./75% RH)), Ambient (25° C./60% RH), Refrig. (refrigerated, 2-8° C.), 3M (3-months).

Based on the above stability data, it is confirmed that there is a significant increase of salamide under accelerated storage (40° C./75% RH). The reason for increasing salamide is hydrolysis of hydrochlorothiazide. This observation is consistent with the reported studies describing hydrolytic degradation of hydrochlorothiazide in aqueous environment irrespective of pH. See, e.g., Connors at 479. Additional observations, not included herein, showed that the rate of hydrolytic degradation is greater in alkali conditions, compared to acidic conditions.

Based on above facts the liquid preparation of hydrochlorothiazide cannot be stored in room temperature for prolonged periods (more than 6 months) and it is not acceptable due to increase in salamide, whose pharmacopoeia limit is NMT 1.0%.

To overcome the hydrolytic degradation issue, a powder for oral suspension was developed, which can be stored under ambient conditions until reconstitution and can be stored under the same conditions after reconstitution until the prescribed date of consumption. Information that follows describes the development activities associated with a powder for oral suspension.

Batches with Powder for Oral Suspension ("PFOS") Approach:

Example 5: Batches with Different Thickening Agent

Hydrochlorothiazide powder for oral suspension 50 mg/5 mL composition with different thickening agents were presented in Table 9.

TABLE 9

Makeup of Formulations 5A-5E

| Ingredients | 5A mg/5 mL | 5B mg/5 mL | 5C mg/5 mL | 5D mg/5 mL | 5E mg/5 mL |
|---|---|---|---|---|---|
| Hydrochlorothiazide | 50.0 | 50.0 | 50.0 | 50.0 | 50.0 |
| Guar gum | 15.0 | — | — | — | — |
| Xanthan gum | — | 15.0 | — | — | — |
| Hypromellose (HPMC 15 cps) | — | — | 20.0 | — | — |
| Avicel RC 591 | — | — | — | 125.0 | — |
| Sodium Carboxymethyl cellulose (Blanose 7 MF) | — | — | — | — | 10.0 |
| Sucrose | 1318.0 | 1321.0 | 1313.0 | 1195.0 | 1310.0 |
| Sodium Benzoate | 5.0 | 5.0 | 5.0 | 5.0 | 5.0 |
| Citric acid anhydrous | 12.0 | 14.0 | 12.0 | 25.0 | 12.0 |
| Total | 1400.0 | 1400.0 | 1400.0 | 1400.0 | 1400.0 |

Brief Manufacturing Procedure:

A 0.42 kg batch was manufactured as follows, hydrochlorothiazide, xanthan gum, guar gum, hypromellose (HPMC 15 cps), Avicel RC 591 (blend of microcrystalline cellulose and carboxymethylcellulose sodium), or sodium carboxymethyl cellulose (Blanose 7 MF) (individual thickening agents were added into their respective batches), sodium benzoate, and citric acid passed through #60mesh. Sucrose was passed through #60mesh and mixed. The remaining quantity of sucrose was passed through #40mesh and blended with above step for 15 min at 15 rpm using V-cone blender. A prepared blend of 36 g was filled in 7.60 oz of white high density polyethylene bottles with 38 mm child resistance closure.

Effect of Gums on Sedimentation

The batches were analyzed for uniformity of dosage unit study. All the individual bottles were reconstituted, shaken well and placed aside for 6 hr. At initial sampling 5 mL suspension were withdrawn from top containers. At every interval 5 mL suspension were withdrawn from top of the container without shaking of container. The samples were analyzed for uniformity of dosage unit.

TABLE 10

Effect of gums on Sedimentation
Hydrochlorothiazide PFOS 50 mg/5 mL
Uniformity of dosage unit

| Time (hr) | 5A | 5B | 5C | 5D | 5E |
|---|---|---|---|---|---|
| Initial | 103.1 | 99.4 | 73.4 | Sedimentation was observed | Sedimentation was observed |
| 1 | 108.3 | 98.9 | 50.9 | | |
| 2 | 118.9 | 99.0 | 48.5 | | |
| 3 | 81.9 | 99.5 | 34.6 | | |
| 6 | 71.7 | 98.8 | 24.5 | | |

Above data shows batches with xanthan gum shows better uniformity of hydrochlorothiazide than other gums containing suspension. Batch with xanthan gum shows no sedimentation of particles for up to 6 hr.

Hydrochlorothiazide powder for oral suspension 50 mg/5 mL composition with minimal number of excipients is presented in below table.

Example 6: Batches with Xanthan Gum

TABLE 11

Makeup of Formulations 6A-6B

| Name of the Ingredient(s) | 6A 50 mg/5 mL | 6B 50 mg/5 mL |
|---|---|---|
| Hydrochlorothiazide | 50.0 | 50.0 |
| Xanthan gum | 15.0 | 15.0 |
| Sucrose | 1122.6 | — |
| Sorbitol | — | 1122.6 |
| Sodium Benzoate | 2.4 | 2.4 |
| Citric acid anhydrous | 10.0 | 10.0 |
| Total | 1200 | 1200 |
| pH | 3.0 | 3.0 |

Brief Manufacturing Procedure:

A 0.83 kg batch was manufactured as follows, hydrochlorothiazide, xanthan gum, sodium benzoate, and citric acid passed through #60mesh. Sucrose/sorbitol was passed through #60mesh and mixed. The remaining quantity of sucrose was passed through #40mesh and blended with above step for 15 min at 15 rpm using V-cone blender. A prepared blend of 36 g was filled in 7.60 oz of white high density polyethylene bottles with 38 mm child resistance closure and stored inverted under various stability conditions.

Batch Wet Granulation Process

TABLE 12

Composition for Powder for oral suspension

| Ingredient(s) | Example No. 6C 50 mg/5 mL |
|---|---|
| Hydrochlorothiazide | 50.0 |
| Xanthan gum | 15.0 |
| Sucrose | 1122.6 |
| Sodium Benzoate | 2.4 |
| Citric acid anhydrous | 10.0 |
| Total | 1200.0 |
| pH | 3.0 |

Brief Manufacturing Procedure:

A 0.86 kg batch was manufactured as follows, hydrochlorothiazide, xanthan gum, and citric acid were passed through #40mesh along with Sucrose was loaded into a high shear mixer granulator ("HSMG") and dry mixed for 15 min with impeller at 350 rpm and chopper off. The blend was granulated using sodium benzoate solution, wet mass was dried at 50° C. until the loss on drying ("LOD") reaches not more than 0.8%. The dried granules are milled using Fitz mill fitted with 1.0 mm (0040) screens, knife forward at 1500 rpm. The milled blend was blended for minutes at 15 rpm in V-blender. A prepared blend of 37.2 g was filled in 7.60 oz of white high density polyethylene bottles with 38 mm child resistance closure and stored inverted under various stability conditions.

Stored samples were analyzed for appearance and pH. pH-values were measured in a manner consistent with USP<791>.

Stored samples also were analyzed for assay (% w/w). The reported amount of hydrochlorothiazide (expressed as Assay (% w/w)) was determined by HPLC with reference to a suitable calibration curve using hydrochlorothiazide USP as reference standard.

Further, stored samples were analyzed for impurities and related substances. Amounts of impurities and related substances were determined by HPLC, as described in, for example, USP 40-NF35 hydrochlorothiazide Monograph.

TABLE 13

Stability Data for Example 10

| | | | Assay | Related Substance (% w/w) | | | | | |
|---|---|---|---|---|---|---|---|---|---|
| FN | Condition | pH | (% w/w) | BTZ RC-A | CRZ | 5-CRZ | HCTZ IMP C | HU | TI |
| | Limit: NMT | | | 1.0 | 0.5 | 0.5 | 0.5 | 0.2 | 1.5 |
| 6A (Blend) | Initial | 3.00 | 101.7 | 0.056 | 0.019 | ND | 0.016 | 0.028 | 0.119 |
| | Accel., 6 M | 3.20 | 101 | 0.067 | 0.017 | ND | 0.016 | 0.045 | 0.228 |
| | Ambient, 6 M | 3.14 | 98.6 | 0.054 | 0.018 | ND | 0.015 | 0.026 | 0.113 |
| | Refrig., 1 M | 3.01 | — | 0.056 | 0.019 | ND | 0.016 | 0.028 | 0.119 |
| 6A (Reconstituted Suspension) | Accel., 46 D | 3.10 | 100.8 | 1.042 | 0.017 | ND | 0.015 | 0.061 | 1.234 |
| | Ambient, 6 M | 3.08 | 101.4 | 0.276 | 0.018 | ND | 0.015 | 0.013 | 0.369 |
| | Refrig., 3 M | — | 102.9 | 0.082 | 0.029 | ND | 0.015 | ND | 0.126 |
| 6C (Blend) | Initial | 3.0 | 102.0 | 0.056 | 0.018 | ND | 0.016 | 0.028 | 0.118 |
| | Accel., 6 M | 3.17 | 103.4 | 0.064 | 0.019 | ND | 0.015 | 0.026 | 0.192 |
| | Ambient, 6 M | 3.17 | 96.1 | 0.056 | 0.019 | ND | 0.015 | 0.029 | 0.119 |
| | Refrig., 1 M | — | — | 0.056 | 0.018 | ND | 0.016 | 0.028 | 0.118 |
| 6C (Reconstituted suspension) | Accel., 44 D | 3.13 | 98.4 | 1.04 | ND | ND | 0.009 | 0.073 | 1.213 |
| | Ambient, 6 M | 3.11 | 96.1 | 0.276 | 0.015 | ND | 0.012 | 0.023 | 0.37 |
| | Refrig., 3 M | — | 100.0 | 0.08 | 0.029 | 0.016 | 0.017 | 0.028 | 0.17 |
| 6B (Blend) | Initial | 3.09 | 100.2 | 0.14 | 0.021 | 0.01 | 0.12 | 0.009 | 0.3 |
| | Accel., 3 M | 3.22 | — | 0.159 | 0.021 | 0.008 | 0.1 | ND | 0.288 |
| | Ambient, 1 M | — | 97.8 | 0.141 | 0.021 | ND | 0.113 | ND | 0.275 |
| | Refrig., 1 M | — | 94.8 | 0.139 | 0.02 | ND | 0.115 | ND | 0.274 |

Abbreviations/Key: FN: Formulation Number, NMT: not more than, ND: not detected, Accel. (accelerated (40° C./75% RH)), Ambient (25° C./60% RH), Refrig. (refrigerated, 2-8° C.), 1M (1-month), 3 M (3-months), 6 M (6-months), 44 D (44-days), 46D (46-days).

Based on the available stability data it is confirmed that the above formulation is stable at 40° C., 25° C. and 2-8° C. and there no significant change in impurity profile particularly salamide but it is increased under accelerated storage (40° C./75% RH) which is reconstituted; hence the powder for oral suspension composition is stable for at least 6 months even under accelerated storage and this formulation can be stored for at least 6 months at room temperature after reconstitution.

TABLE 14

Makeup of Formulations 6D and 6E

| | Formulation No. | |
|---|---|---|
| | 6D | 6E |
| Ingredient | 50 mg/5 mL | 50 mg/5 mL |
| Hydrochlorothiazide | 50.0 | 50.0 |
| Xanthan gum | 15.0 | 15.0 |
| Sucrose | 1323 | 1328 |
| Sodium Benzoate | 5 | 5 |
| Citric acid anhydrous | 7 | 2 |
| Total | 1400 | 1400 |
| pH | 3.5 | 4.5 |

Brief Manufacturing Procedure:

A 0.56 kg batch was manufactured as follows, hydrochlorothiazide, xanthan gum, and citric acid were passed through #40mesh along with sucrose was loaded into HSMG and dry mixed for 15 minutes with impeller at 350 rpm and chopper off. The blend was granulated using sodium benzoate solution; wet mass was dried at 50° C. until the LOD reaches not more than 0.8%. The dried granules are milled using Fitz mill fitted with 1.0 mm (0040) screens, knife forward at 1500 rpm. The milled blend was blended for 5 minutes at 15 rpm in V-blender. A prepared blend of 14.0 g was filled in glass bottles and stored inverted under various stability conditions.

TABLE 15

Stability Data for Formulations 6D and 6E

| FN | Condition | Assay (% w/w) Limit: NMT (% w/w) | BTZ RC-A 1.0 | CRZ 0.5 | 5-CRZ 0.5 | HCTZ IMP C 0.5 | HU 0.2 | TI 1.5 |
|---|---|---|---|---|---|---|---|---|
| 6D (Blend) | Initial | 97.8 | 0.178 | 0.020 | ND | 0.104 | ND | 0.302 |
| | Accel., 3 M | 95 | 0.201 | 0.020 | 0.008 | 0.089 | ND | 0.318 |
| | Ambient, 3 M | 94.6 | 0.202 | 0.019 | 0.008 | 0.095 | ND | 0.324 |
| 6E (Blend) | Initial | 99 | 0.140 | 0.025 | ND | 0.118 | ND | 0.283 |
| | Accel., 3 M | 99 | 0.140 | 0.025 | ND | 0.118 | ND | 0.283 |
| | Ambient, 3 M | 98.3 | 0.126 | 0.022 | 0.009 | 0.093 | 0.012 | 0.262 |

Abbreviations/Key: FN: Formulation Number, NMT: not more than, Accel. (accelerated (40° C./75% RH)), Ambient (25° C./60% RH), Refrig. (refrigerated, 2-8° C.), 3 M (3-months).

Based on the available stability data it is confirmed that the above formulation is stable under accelerated (40° C./75% RH), ambient (25° C./60% RH), and refrigerated (2-8° C.) conditions and there is no significant change in impurity profile—particularly salamide. It should be noted that salamide increased under accelerated condition at 40° C./75% RH after reconstitution; hence the powder for oral suspension composition is stable at least 6 months even in accelerated condition and this formulation can be stored at least 6 months at room temperature after reconstitution.

Example 7: Additional Batches and Bioequivalence Study

| | mg/5 mL | |
|---|---|---|
| Ingredient | 7A | 7B |
| Hydrochlorothiazide | 50.00 | 50.00 |
| Sucrose | 1280.50 | 1312.00 |
| Xanthan gum | 17.50 | 15.00 |
| Sodium Benzoate | 2.50 | 2.50 |
| Citric acid anhydrous | 14.00 | 14.00 |
| Sucralose | 3.00 | 3.00 |
| Peppermint flavor | 0.50 | 0.50 |
| Caramel flavor | 30.00 | 1.00 |
| Talc | 2.00 | 2.00 |
| Total weight | 1400.00 | 1400.00 |

Manufacturing Process for 7A

A 22.4 kg batch was manufactured as follows, hydrochlorothiazide, xanthan gum, and citric acid were passed through #40 mesh along with sucrose was loaded into a high shear mixer granulator ("HSMG") and dry mixed for 15 min with impeller at 350 rpm and chopper off. The blend was granulated using sodium benzoate solution, wet mass was dried at 50° C. until the loss on drying ("LOD") reaches not more than 0.8%. The dried granules are milled using Fitz mill fitted with 1.0 mm (0040) screens, knife forward at 1500 rpm. The milled blend was blended with #30mesh passed sucralose, peppermint, caramel flavor and talc for 5 minutes at 15 rpm in V-blender.

Manufacturing Process for 7B

A 2.69 kg batch was manufactured as follows, hydrochlorothiazide, xanthan gum, and citric acid were passed through #40mesh along with sucrose was loaded into a high shear mixer granulator ("HSMG") and dry mixed for 15 min with impeller at 350 rpm and chopper off. The blend was granulated using sodium benzoate solution, wet mass was dried at 50° C. until the loss on drying ("LOD") reaches not more than 0.8%. The dried granules are milled using Fitz mill fitted with 1.0 mm (0040) screens, knife forward at 1500 rpm. The milled blend was blended with #30mesh passed sucralose, peppermint, raspberry flavor and talc for 5 minutes at 15 rpm in V-blender.

The powder for oral suspension for oral administration described in Examples 7A and 7B were reconstituted in water in an amount suitable to the desired doses per bottle. For instance, a bottle comprising 10 doses comprises about 14 g of the powder to which about 40 mL of water is added to obtain a final volume of about 50 mL of oral liquid suspension having an HCTZ concentration of about 50 mg/5 mL (or about 1 mg/mL).

Hydrochlorothiazide available in various dosage forms like tablets and capsules in USA. Reference listed drug product of Hydrochlorothiazide Tablets is approved in U.S prior to Jan. 1, 1982 (Applicant: Ivax Pharmaceuticals Inc Sub Teva Pharmaceuticals USA). See HCTZ Tablets Prescribing Information. It is available in the strengths of 12.5 mg, 25 mg and 50 mg. Hydrochlorothiazide Tablets (or "Reference") includes 50 mg HCTZ, corn starch, dibasic calcium phosphate dihydrate, FD&C Yellow No. 6 Aluminum, lactose monohydrate, and magnesium stearate.

A bioequivalence study was conducted by an open labelled, balanced, randomized, three-treatment, three-period, three-sequence, three-way crossover, single dose, oral bioequivalence study of 2 test products of Hydrochlorothiazide Powder for Oral Suspension 50 mg per 5 mL (Ex. 7A and Ex. 7B) compared with Hydrochlorothiazide Tablets 50 mg (Reference) in healthy adult male subjects under fasting conditions. Table 16 provides relevant pharmacokinetic parameters for liquid oral suspensions obtained by reconstituting the powders disclosed herein (e.g., Ex. 7A and Ex. 7B) in a suitable amount of a water to obtain an HCTZ concentration of 50 mg/5 mL with subjects receiving a 5 mL dose of the 50 mg HCTZ/5 mL liquid oral suspension (Test) or 50 mg of the Hydrochlorothiazide Tablets (Reference).

TABLE 16

Statistical Results of Hydrochlorothiazide (Ex. 7A Vs Reference)

| Parameters (Units) | Geometric Least Square mean (Geometric SD) | | Ratio (%) |
|---|---|---|---|
| | Test | Reference | |
| $C_{max}$ (ng/mL) | 368.8235 (1.2848) | 305.5959 (1.3229) | 120.69% |
| $AUC_{0-t}$ (hr * ng/mL) | 2311.9705 (1.2845) | 2139.5828 (1.2676) | 108.06% |
| $AUC_{0-\infty}$ (hr * ng/mL) | 2463.5469 (1.2693) | 2265.2431 (1.2648) | 108.75% |

| Parameters (Units) | 90% Confidence Intervals | Acceptance Criteria | Outcome of BE result |
|---|---|---|---|
| $C_{max}$ (ng/mL) | 108.25% to 134.55% | 80.00%-125.00% | Not Bioequivalent |
| $AUC_{0-t}$ (hr * ng/mL) | 100.24% to 116.49% | 80.00%-125.00% | |
| $AUC_{0-\infty}$ (hr * ng/mL) | 101.01% to 117.09% | 80.00%-125.00% | |

TABLE 17

Statistical Results of Hydrochlorothiazide (Ex. 7B Vs Reference)

| Parameters (Units) | Geometric Least Square mean (Geometric SD) | | Ratio (%) |
|---|---|---|---|
| | Test | Reference | |
| $C_{max}$ (ng/mL) | 309.1389 (1.2310) | 305.5959 (1.3229) | 101.16% |
| $AUC_{0-t}$ (hr * ng/mL) | 2164.2335 (1.2863) | 2139.5828 (1.2676) | 101.15% |
| $AUC_{0-\infty}$ (hr * ng/mL) | 2291.7964 (1.2734) | 2265.2431 (1.2648) | 101.17% |

| Parameters (Units) | 90% Confidence Intervals | Acceptance Criteria | Outcome of BE result |
|---|---|---|---|
| $C_{max}$ (ng/mL) | 90.74% to 112.78% | 80.00%-125.00% | Bioequivalent |
| $AUC_{0-t}$ (hr * ng/mL) | 93.83% to 109.04% | 80.00%-125.00% | |
| $AUC_{0-\infty}$ (hr * ng/mL) | 93.97% to 108.93% | 80.00%-125.00% | |

Conclusion:

Based on the results of the bioequivalence study, of Hydrochlorothiazide Powder for Oral Suspension (Ex. 7B) 50 mg per 5 mL found to be bioequivalent with reference product of Hydrochlorothiazide tablets 50 mg. Similar bioequivalence results may be achieved for an additional powder for oral suspension disclosed herein (e.g., Ex. 6C). For instance, administration of a dose (e.g., 50 mg HCTZ/5 mL) to a human subject of an oral liquid suspension comprising the powder of any one of the oral suspensions disclosed herein (e.g., Exs. 6C, 7A, 7B, etc.) and a pharmaceutically acceptable carrier comprising water provides a geometric least squares mean for $C_{max}$ of from about 300 ng/mL to about 400 ng/mL, a geometric least squares mean for $AUC_{0-\infty}$ of from about 2200 ng•hr/mL to about 2500 ng•hr/mL, or a combination thereof.

Example 8: Additional Batches and Bioequivalence Study

| Ingredient | mg/5 mL |
|---|---|
| Hydrochlorothiazide | 50.00 |
| Sucrose | 1274.00 |
| Sucralose | 4.00 |
| Potassium Sorbate | 15.00 |
| Citric acid anhydrous | 8.00 |
| Caramel flavour | 2.50 |
| Powdered Cellulose | 7.00 |
| Xanthan gum | 25.00 |
| Peppermint flavour | 0.50 |
| Talc | 14.0 |
| Total weight | 1400.00 |
| pH | 4.5 |

Manufacturing Process:

Granulation:

Hydrochlorothiazide, sucrose, sucralose, potassium sorbate, citric acid anhydrous, caramel flavor, powdered cellulose were passed through #30 mesh and loaded to 75L Gral and dry mixed for 5 minutes with impeller and chopper slow speeds. The dry mix was granulated by spraying with water for 3 minutes and mixed additional 20 seconds with impeller and chopper slow speeds. The wet granules were dried in dray dryer set at 50° C.±5° C. for 30 minutes and raked and again dried for 1 hour. The dried granules were milled in fitzmil with 1512 0020 screens at medium speed. The Xanthan gum, Peppermint flavor were passed through #30 mesh screen and added into 3 Cu Ft V blender along with milled granules and mixed for 10 minutes. Talc was screened and added into V blended and mixed for 5 minutes. The final blend was filled into bottles using Allfill powder filling machine with fill weight of 22.4 g±5% (reconstitute with 600 mL of water).

The stability of above reconstituted powder for solution formulation of hydrochlorothiazide was checked in terms of viscosity and results are tabulated below.

TABLE 18

Stability of HCTZ PFOS (Example 8) 50 mg/5 mL in terms of viscosity HCTZ PFOS 50 mg/5 mL-Viscosity, cP

| Composition | Condition | 30 RPM Torque (%) | 30 RPM Viscosity (cP) | 60 RPM Torque (%) | 60 RPM Viscosity (cP) |
|---|---|---|---|---|---|
| 125 mL Glass bottle/28 mm CR Cap | Initial | 46 | 142.6 | 53.5 | 82.94 |
| | 25° C./60% RH 3M | 43.8 | 135.8 | 51.4 | 79.69 |
| | 25° C./60% RH 6M | 48.3 | 149.8 | 49 | 75.97 |
| | 40° C./75% RH 3M | 50.4 | 156.3 | 56.9 | 88.21 |
| | 40° C./75% RH 6M | 49.8 | 154.4 | 39.7 | 61.55 |
| Thickwall HDPE Bottle/ 28 mm CR Cap | 25° C./60% RH 3M | 48 | 148.8 | 56 | 86.82 |
| | 25° C./60% RH 6M | 59.5 | 184.5 | 59.8 | 92.71 |
| | 40° C./75% RH 3M | 56.6 | 175.5 | 65.9 | 102.2 |
| | 40° C./75% RH 6M | 66.9 | 207.4 | 52.5 | 81.39 |

Observation:

The viscosity results are satisfactory in long-term and accelerated conditions for at least 6 months for the above powder for solution formulation of hydrochlorothiazide.

TABLE 19

Stability Data for HCTZ PFOS (Example 8) 50 mg/5 ml
Related Substance (% w/w)

| FN | Composition | Condition | pH | Assay (% w/w) | BTZ RC-A 1.0 | CRZ 0.5 | HU 0.2 | TI 1.5 |
|---|---|---|---|---|---|---|---|---|
| | | Limit(s): NMT (w/w %) | | | | | | |
| 8 | 125 mL Glass bottle/28 mm CR Cap | Initial | 4.55 | 100.3 | 0.101 | 0.021 | ND | 0.122 |
| | | 40° C./75% RH-1 M | | | 0.064 | 0.013 | ND | 0.077 |
| | | 40° C./75% RH-3 M | | 103.2 | 0.077 | ND | ND | 0.077 |
| | | 40° C./75% RH-6 M | 4.47 | 105.4 | 0.205 | ND | 0.177 | 0.3948 |
| | | 25° C./60% RH-3 M | | 101 | 0.252 | ND | ND | 0.0252 |
| | | 25° C./60% RH-6 M | 4.54 | 105.8 | 0.1777 | ND | 0.187 | 0.4008 |
| 8 | Thickwall HDPE Bottle/ 28 mm CR Cap | Initial | 4.55 | 101.4 | 0.101 | 0.021 | ND | 0.122 |
| | | 40° C./75% RH-1 M | | | 0.061 | 0.026 | ND | 0.087 |
| | | 40° C./75% RH-3 M | | 102.1 | 0.074 | ND | ND | 0.074 |
| | | 40° C./75% RH-6 M | 4.55 | 108.1 | 0.2238 | ND | 0.176 | 0.4123 |
| | | 25° C./60% RH-3 M | | 102.4 | 0.056 | ND | ND | 0.056 |
| | | 40° C./75% RH-6 M | 4.53 | 106.7 | 0.1819 | ND | 0.183 | 0.3649 |

Observation:

Based on the above stability data it is confirmed that the above formulation is stable under accelerated (40° C./75% RH) and ambient (25° C./60% RH) conditions for at least 6 months and all the impurities are under acceptable limit particularly salamide impurity. It should be noted that salamide increased under accelerated condition at 40° C./75% RH after reconstitution; hence the powder for oral suspension composition is stable at least 6 months even in accelerated condition and this formulation can be stored at least 1 month at room temperature after reconstitution.

Bioequivalence (BE) Study for HCTZ PFOS (Example 8) 50 mg/5 mL:

A bioequivalence study was conducted by an open labelled, balanced, randomized, three-treatment, three-period, three-sequence, three-way crossover, single dose, oral bioequivalence study of 2 test products of Hydrochlorothiazide Powder for Oral Suspension 50 mg per 5 mL (T1 and T2) compared with Hydrochlorothiazide Tablets 50 mg (Reference) in healthy adult male subjects under fasting conditions. Table 20 provides relevant pharmacokinetic parameters for liquid oral suspensions obtained by reconstituting the powders disclosed herein (Example-8) in a suitable amount of a water to obtain an HCTZ concentration of 50 mg/5 mL with subjects receiving a 5 mL dose of the 50 mg HCTZ/5 mL liquid oral suspension (T1 and T2) or 50 mg of the Hydrochlorothiazide Tablets (Reference).

In bioequivalence (BE) study, a single dose of two test formulations of the hydrochlorothiazide oral suspension (50 mg/5 mL; T1 and T2) was compared against a single dose of the reference listed drug (RLD), HCT tablets USP (50 mg; R), in 18 healthy human adult male subjects (ages 18-45 years) under fasting conditions. Each subject was randomized to receive the investigational product (in one of the three sequences: either T1T2R or T2RT1 or RT1T2, over the course of 18 days (three periods), with at least a seven-day washout period between each drug administration. In each period, a total of 24 venous blood samples were collected at pre-dose up until 48 hours post dose.

TABLE 20

Statistical Results of Hydrochlorothiazide (Ex. 8 Vs Reference)
(Hydrochlorothiazide Powder for Oral Suspension 50 mg/5 ml)
Results of Mean ± SD (CV %), ISCV, 90% Confidence Intervals of Test versus Reference
product based on Ln-transformed data for Hydrochlorothiazide (N = 17)

| Parameters (Units) | Mean ± SD (CV %) | | | Ratio (%) | | |
|---|---|---|---|---|---|---|
| | Test (T1) | Test (T2) | Reference (R) | T1/R | T2/R | ISCV (%) |
| $C_{max}$ (ng/ml) | 381.814 ± 97.1555 (25.45%) | 313.611 ± 54.8706 (17.50%) | 317.566 ± 91.7431 (28.89%) | 120.69% | 101.16% | 18.81% |
| $AUC_{0-t}$ (hr*ng/mL) | 2391.787 ± 515.3607 (21.55%) | 2222.884 ± 496.7173 (22.35%) | 2205.686 ± 524.1866 (23.77%) | 108.06% | 101.15% | 12.93% |
| $AUC_{0-\infty}$ (hr*ng/ml) | 2544.084 ± 537.3631 (21.12%) | 2349.747 ± 509.3941 (21.68%) | 2333.910 ± 544.2918 (23.32) | 108.75% | 101.17% | 12.72% |

| Parameters (Units) | 90% C.I for T1 vs R | 90% C.I for T2 vs R | Acceptance Criteria | Outcome of BE result |
|---|---|---|---|---|
| $C_{max}$ (ng/ml) | 108.25% to 134.55% | 90.74% to 112.78% | 80.00%-125.00% | Not Bioequivalent (T1 Vs R) Bioequivalent (T2 Vs R) |
| $AUC_{0-t}$ (hr*ng/ml) | 100.24% to 116.49% | 93.83% to 109.04% | 80.00%-125.00% | |
| $AUC_{0-\infty}$ (hr*ng/mL) | 101.01% to 117.09% | 93.97% to 108.93% | 80.00%-125.00% | |

Based on the results of the bioequivalence study, the hydrochlorothiazide Powder for Oral Suspension (Ex. 8) 50 mg per 5 mL was found to be bioequivalent with reference product of hydrochlorothiazide tablets 50 mg. For instance, administration of a dose (e.g., 50 mg HCTZ/5 mL) to a human subject of an oral liquid suspension comprising the powder of oral suspensions disclosed herein and a pharmaceutically acceptable carrier comprising water provides a geometric least squares mean for $C_{max}$ of from about 300 ng/mL to about 400 ng/mL, a geometric least squares mean for $AUC_{0-\infty}$ of from about 2300 ng•hr/mL to about 2600 ng•hr/mL, or a combination thereof.

The pharmacokinetic analysis demonstrated that the mean T1 maximum measured plasma concentration ($C_{max}$) of 381.81±97 nanograms per milliliter (ng/mL; with mean $T_{max}$ [time of maximum concentration] value of 1.46 hours) was higher than the mean RLD tablet $C_{max}$ of 317.57±91 ng/mL ($T_{max}$ mean value of 2.39 hours). The mean T2 $C_{max}$ was slightly lower (313.61±55 ng/mL; $T_{max}$ mean value of 1.52 hours) than the mean RLD tablet $C_{max}$. The present inventor has evaluated the T1 HCT $C_{max}$ to determine if the elevated $C_{max}$ plasma concentrations for the proposed oral suspension formulation are safe.

Based on pharmacokinetic evaluation it is concluded that though the T1 mean $C_{max}$ value for the proposed oral suspension formulation in the BE study is higher than the RLD tablet $C_{max}$ value, there is no indication that this elevated plasma level is overall inconsistent with the maximum 50 mg oral tablet dose plasma levels observed in the literature, and is well within plasma levels that do not cause adverse effects and are known to be safe.

Additional Aspects

Aspect 1. A powder for oral suspension for oral administration, comprising about 3% w/w to about 5% w/w of hydrochlorothiazide; at least one thickening agent; and at least one pharmaceutically acceptable excipient; wherein the powder for oral suspension composition in 5 mL of water has a pH of from about 3.5 to about 5.5.

Aspect 2. The powder of Aspect 1 comprising about 3.2% w/w to about 4.2% w/w of hydrochlorothiazide.

Aspect 3. The powder of any one of Aspects 1-2 comprising about 3.6% w/w of hydrochlorothiazide.

Aspect 4. The powder of any one of Aspects 1-3 having a water content of not more than about 0.8% w/w.

Aspect 5. The powder of any one of Aspects 1-4, wherein at least one thickening agent selected from hydrocolloid gum, cellulosic derivative, a polysaccharide, alginate, acrylic acid copolymer, polyvinylpyrrolidone, aluminium magnesium silicate, and a combination thereof.

Aspect 6. The powder of any one of Aspects 1-5, wherein the amount of thickening agent in an amount of from about 0.4% w/w to about 5% w/w.

Aspect 7. The powder of any one of Aspects 1-6, wherein the thickening agent comprises xanthan gum in an amount of from about 0.4% w/w to about 2.5% w/w.

Aspect 8. The powder of any one of Aspects 1-7, wherein the at least one pharmaceutically acceptable excipient comprises a preservative and a sweetener.

Aspect 9. The powder of any one of Aspects 1-8, wherein the at least one pharmaceutically acceptable excipient comprises a preservative selected from the group consisting of sodium benzoate, benzoic acid, potassium sorbate, paraben, methylparaben, ethylparaben, propylparaben, butylparaben, isobutylparaben, benzyl alcohol, boric acid, calcium acetate, bentonite, cetrimide, chlorhexidine, cetylpyridinium chloride, cresol, chlorbutanol, magnesium trisilicate, and a combination thereof.

Aspect 10. The powder of any one of Aspects 1-9, wherein the at least one pharmaceutically acceptable excipient comprises a preservative selected from the group consisting of sodium benzoate, benzoic acid, potassium sorbate, paraben, methylparaben, ethylparaben, propylparaben, butylparaben, isobutylparaben, benzyl alcohol, boric acid, calcium acetate, bentonite, cetrimide, chlorhexidine, cetylpyridinium chloride, cresol, chlorbutanol, magnesium trisilicate, and combination thereof in an amount of from about 0.01% w/w to about 5% w/w.

Aspect 11. The powder of any one of Aspects 1-10, wherein the at least one pharmaceutically acceptable excipient comprises a sweetener selected from the group consisting of sucralose, maltilol, liquid glucose, magnasweet 110, magnasweet 180, saccharin sodium, xylitol, sorbitan monoleate, sorbitol, sucrose, aspartame, acesulfame potassium, and a combination thereof.

Aspect 12. The powder of any one of Aspects 1-11, wherein the at least one pharmaceutically acceptable excipient comprises a sweetener selected from the group consisting of sucralose, maltilol, liquid glucose, magnasweet 110, magnasweet 180, saccharin sodium, xylitol, sorbitan monoleate, sorbitol, sucrose, aspartame, acesulfame potassium, and a combination thereof in an amount of from about 0.1% w/w to about 96% w/w.

Aspect 13. The powder of any one of Aspects 1-2, wherein the at least one pharmaceutically acceptable excipient comprises a sweetener selected from the group consisting of sucralose, sucrose, and a combination thereof in an amount of from about 90% w/w to about 96% w/w.

Aspect 14. The powder of any one of Aspects 1-13, wherein the at least one pharmaceutically acceptable excipient comprises a pH modifier selected from group consisting of citric acid, fumaric acid, tartaric acid, malic acid, sodium phosphate monobasic, potassium phosphate, maleic acid, lactic acid, hydrochloric acid, phosphoric acid, and a combination thereof.

Aspect 15. The powder of any one of Aspects 1-4, wherein the at least one pharmaceutically acceptable excipient comprises a pH modifier selected from group consisting of citric acid, fumaric acid, tartaric acid, malic acid, sodium phosphate monobasic, potassium phosphate, maleic acid, lactic acid, hydrochloric acid, phosphoric acid, and a combination thereof in an amount of from about 0.2% w/w to about 1.2% w/w.

Aspect 16. The powder of any one of Aspects 1-15, having a salamide impurity content not more than 1.0% for at least about 6-months when stored at 25±2° C. and 60±5% relative humidity, 40° C. and 75% relative humidity and a salamide impurity content not more than 1.0% for at least about 6-months when stored at 25±2° C. and 60±5% relative humidity after reconstitution.

Aspect 17. An oral liquid suspension comprising the powder of any one of Aspects 1-16 a pharmaceutically acceptable carrier comprising water.

Aspect 18. The oral liquid suspension of Aspect 17 having a volume of from about 50 mL to about 150 mL.

Aspect 19. A method of treating edema and hypertension comprising administering to a patient in need thereof a therapeutically effective amount of the oral liquid suspension of any one of Aspects 17-18.

Aspect 20. The method of Aspect 19, wherein administration of the oral liquid suspension to the human patient provides a geometric least squares mean for $C_{max}$ of from about 200 ng/mL to about 450 ng/mL, a geometric least squares mean for $AUC_{0-\infty}$ of from about 1800 ng•hr/mL to about 2900 ng•hr/mL, or a combination thereof.

Cited Information

Barbhaiya et al. *Comparative bioavailability and pharmacokinetics of hydrochlorothiazide from oral tablet dosage forms, determined by plasma level and urinary excretion methods*, Biopharmaceutics and Drug Disposition (1982) 3(4): 329-336.

Beermann et al., *Pharmacokinetics of hydrochlorothiazide in man*, European Journal of Clinical Pharmacology (1977) 12(4): 297-303.

Bercu et al., *Potential impurities in drug substances: Compound-specific toxicology limits for 20 synthetic reagents and by-products, and a class-specific toxicology limit for alkyl bromides*, Regulatory Toxicology and Pharmacology (2018) 94: 172-182 ("Bercu").

Binson et al., *Preparation and Physicochemical Stability of Liquid Oral Dosage Forms Free of Potentially Harmful Excipient Designed for Pediatric Patients*, Pharmaceutics (2019) 11(190): 1-13 ("Binson").

CAS Registry No. 121-30-2 for Salamide ("BTZ RC-A") (2021).

CAS Registry No. 58-94-6 for Chlorthiazide (CRZ) (2021).

CAS Registry No. 5233-42-1 for 5-chloro-hydrochlorozide ("5-CRZ") (2021).

CAS Registry No. 402824-96-8 for HCTZ Related Compound C (2021).

Cirri et al., *Development of a stable oral pediatric solution of hydrochlorothiazide by the combined use of cyclodextrins and hydrophilic polymers*, International Journal of Pharmaceutics (2020) 587 (25) 119692, 1-9 ("Cirri").

Connors et al., *Chemical Stability of Pharmaceuticals: A Handbook for Pharmacists*, 2nd Ed. (1986), pp. 345-350 and 478-482 ("Connors").

Deppler, H. P. *Hydrochlorthiazide*, Analytical Profiles of Drug Substances (1981) 10: 405-440 ("Deppler").

Desai et al., *Effects of different types of lactose and disintegrant on dissolution stability of hydrochlorothiazide capsule formulations*, International Journal of Pharmaceutics (1994) 110 (3) 257-265 ("Desai").

Devineni et al., *Effects of hydrochlorothiazide on the pharmacokinetics, pharmacodynamics, and tolerability of canagliflozin, a sodium glucose co-transporter 2 inhibitor, in healthy participants*, Clinical Therapeutics (2014) 35(5): 698-710.

European Paediatric Formulary, *Hydrochlorothiazide 0.5 mg/mL Oral Solution* Product Description (2019) ("HCTZ (0.5 mg/mL) Product Information").

European Pharmacopoeia 5.0, Hydrochlorothiazide (2015), pp. 1756-1757 ("EP 5.0").

Hydrochlorothiazide Tablets USP Prescribing Information by Teva Pharmaceuticals USA, Inc. (2020) ("HCTZ Tablets Prescribing Information").

Jacob et al., *A toxicity assessment of 30 pharmaceuticals using Aliivibrio fischeri: a comparison of the acute effects of different formulations*, Environmental Technology (2016) 37(21) 2760-2767 ("Jacob").

Li, Y. Y., *Development of a Hydrochlorothiazide 0.5 mg/mL Oral Solution for Children*, Eur J Hosp Pharm (2013) 20(Suppl 1): A71 ("Li").

Mendes et al., Physicochemical and microbiological stability studies of extemporaneous antihypertensive pediatric suspensions for hospital use, Pharmaceutical Development and Technology (2013) 18(4): 813-820 ("Mendes").

Mexican Patent No. 354316 B, *Pharmaceutical composition with an antihypertensive and diuretic*, granted on Feb. 26, 2018 to Hernandez et al. of Sensosiain Laboratorios ("Hernandez").

Niemeyer et al., *Pharmacokinetics of hydrochlorothiazide in relation to renal function*, European Journal of Clinical Pharmacology (1983) 24(5): 661-665.

Patel et al., *Bioavailability of Hydrochlorothiazide from Tablets and Suspensions*, Journal of Pharmaceutical Sciences (1984) 73(3) 359-361 ("Patel 1984").

Patel et al., *Development and evaluation of in situ novel intragastric controlled-release formulation of hydrochlorothiazide*, Acta Pharm. (2011) 61: 73-82 ("Patel 2011").

Redalieu et al., *Determination of plasma hydrochlorothiazide levels in humans*, Journal of Pharmaceutical Sciences (1978) 67(5): 726-728.

Santoveria et al., *Design of a pediatric oral formulation with a low proportion of hydrochlorothiazide*, International Journal of Pharmaceutics (2012) 423(2): 360-364 ("Santoveria").

Shah et al., *In Vitro Release of Hydrochlorothiazide from Capsule Formulations*, Drug Development and Industrial Pharmacy (1981) 7(6): 683-691 ("Shah").

Tagliari et al., *Evaluation of physicochemical characteristics of suspensions containing hydrochlorothiazide developed for pediatric use*, Lat. Am. J. Pharm. (2009) 28(5): 734-740 ("Tagliari").

The United States Pharmacopeia, Hydrochlorothiazide (2005), pp. 954-955 ("USP 2005").

U.S. Pat. No. 2,809,194, *Thiadiazine Type Natriuretic Agents*, issued on Oct. 8, 1957 to Frederick C. Novello of Merck & Co., Inc. ("Novello").

U.S. Pat. No. 4,981,852, *Chemical Compounds Triamterene and Hydrochlorothiazide*, issued on Jan. 1, 1991 to Kap S. Ahn of Multilan AG ("Ahn"); corresponding to EP Patent Application Publication No. 0 341 774 A1.

Williams et al., *Hydrochlorothiazide pharmacokinetics and pharmacologic effect: the influence of indomethacin*, The Journal of Clinical Pharmacology (1982) 22(1): 32-41.

The subject matter of U.S. patent application Ser. No. 17/546,175 filed on Dec. 9, 2021 is incorporated by reference in its entirety. Additionally, the subject matter of Indian Patent Application No. 202041053842, filed on Dec. 10, 2020, is incorporated by reference in its entirety. Further, the subject matter of the documents cited herein is incorporated by reference in their entirety to the extent necessary. If there is a difference in meaning between the incorporated terms and the terms disclosed herein, the meaning of the terms disclosed herein will control.

Those skilled in the art will also appreciate that various adaptations and modifications of the preferred and alternative embodiments described above can be configured without departing from the scope and spirit of the disclosure. Therefore, it is to be understood that, within the scope of the appended claims, the disclosure may be practiced other than as specifically described herein.

The invention claimed is:

1. A powder for oral suspension for oral administration, comprising
   about 3% w/w to about 5% w/w of hydrochlorothiazide;
   at least one thickening agent; and
   at least one pharmaceutically acceptable excipient;
   wherein the powder for oral suspension composition in 5 mL of water has a pH of from about 3.5 to about 5.5.

2. The powder of claim 1 comprising about 3.5% w/w to about 4.4% w/w of hydrochlorothiazide.

3. The powder of claim 1 comprising about 4.2% w/w of hydrochlorothiazide.

4. The powder of claim 1 having a water content of not more than about 0.8% w/w.

5. The powder of claim 1, wherein the at least one thickening agent is selected from hydrocolloid gum, cellulosic derivative, a polysaccharide, alginate, acrylic acid copolymer, polyvinylpyrrolidone, aluminium magnesium silicate, and a combination thereof.

6. The powder of claim 1, wherein the amount of the at least one thickening agent is in an amount of from about 0.4% w/w to about 5% w/w.

7. The powder of claim 1, wherein the at least one thickening agent comprises xanthan gum in an amount of from about 0.4% w/w to about 2.5% w/w.

8. The powder of claim 1, wherein the at least one pharmaceutically acceptable excipient comprises a preservative and a sweetener.

9. The powder of claim 1, wherein the at least one pharmaceutically acceptable excipient comprises a preservative selected from the group consisting of sodium benzoate, benzoic acid, potassium sorbate, paraben, methylparaben, ethylparaben, propylparaben, butylparaben, isobutylparaben, benzyl alcohol, boric acid, calcium acetate, bentonite, cetrimide, chlorhexidine, cetylpyridinium chloride, cresol, chlorbutanol, magnesium tri silicate, and a combination thereof.

10. The powder of claim 1, wherein the at least one pharmaceutically acceptable excipient comprises a preservative selected from the group consisting of sodium benzoate, benzoic acid, potassium sorbate, paraben, methylparaben, ethylparaben, propylparaben, butylparaben, isobutylparaben, benzyl alcohol, boric acid, calcium acetate, bentonite, cetrimide, chlorhexidine, cetylpyridinium chloride, cresol, chlorbutanol, magnesium trisilicate, and combination thereof in an amount of from about 0.01% w/w to about 5% w/w.

11. The powder of claim 1, wherein the at least one pharmaceutically acceptable excipient comprises a sweetener selected from the group consisting of sucralose, maltilol, liquid glucose, magnasweet 110, magnasweet 180, saccharin sodium, xylitol, sorbitan monoleate, sorbitol, sucrose, aspartame, acesulfame potassium, and a combination thereof.

12. The powder of claim 1, wherein the at least one pharmaceutically acceptable excipient comprises a sweetener selected from the group consisting of sucralose, maltilol, liquid glucose, magnasweet 110, magnasweet 180, saccharin sodium, xylitol, sorbitan monoleate, sorbitol, sucrose, aspartame, acesulfame potassium, and a combination thereof in an amount of from about 0.1% w/w to about 96% w/w.

13. The powder of claim 1, wherein the at least one pharmaceutically acceptable excipient comprises a sweetener selected from the group consisting of sucralose, sucrose, and a combination thereof in an amount of from about 90% w/w to about 96% w/w.

14. The powder of claim 1, wherein the at least one pharmaceutically acceptable excipient comprises a pH modifier selected from group consisting of citric acid, fumaric acid, tartaric acid, malic acid, sodium phosphate monobasic, potassium phosphate, maleic acid, lactic acid, hydrochloric acid, phosphoric acid, and a combination thereof.

15. The powder of claim 1, wherein the at least one pharmaceutically acceptable excipient comprises a pH modifier selected from group consisting of citric acid, fumaric acid, tartaric acid, malic acid, sodium phosphate monobasic, potassium phosphate, maleic acid, lactic acid, hydrochloric acid, phosphoric acid, and a combination thereof in an amount of from about w/w to about 1.2% w/w.

16. The powder of claim 1, having a salamide impurity content not more than 1.0% for at least about 6-months when stored at 25±2° C. and 60±5% relative humidity, 40° C. and 75% relative humidity and a salamide impurity content not more than 1.0% for at least about 6-months when stored at 25±2° C. and 60±5% relative humidity after reconstitution.

17. An oral liquid suspension comprising the powder of claim 1 and a pharmaceutically acceptable carrier comprising water.

18. The oral liquid suspension of claim 17 having a volume of from about 50 mL to about 150 mL.

19. A method of treating edema and hypertension comprising administering to a patient in need thereof a therapeutically effective amount of the oral liquid suspension of claim 17.

20. The method of claim 19, wherein administration of the oral liquid suspension to the human patient provides a geometric least squares mean for $C_{max}$ of from about 200 ng/mL to about 450 ng/mL, a geometric least squares mean for $AUC_{0-\infty}$ of from about 1800 ng•hr/mL to about 2900 ng•hr/mL, or a combination thereof.

* * * * *